United States Patent
Meul et al.

(10) Patent No.: US 10,723,691 B2
(45) Date of Patent: Jul. 28, 2020

(54) PROCESS FOR PREPARING SALICYLOYL-L-CARNITINE HYDROCHLORIDE

(71) Applicant: DRUG'ON PHARMA SWITZERLAND AG, Liestal (CH)

(72) Inventors: Thomas Meul, Visp (CH); Peter Weber, Birsfelden (CH)

(73) Assignee: DRUG'ON PHARMA SWITZERLAND AG, Liestal (CH)

( * ) Notice: Subject to any disclaimer, the term of this patent is extended or adjusted under 35 U.S.C. 154(b) by 0 days.

(21) Appl. No.: 16/329,132

(22) PCT Filed: Aug. 29, 2017

(86) PCT No.: PCT/EP2017/071608
§ 371 (c)(1),
(2) Date: Feb. 27, 2019

(87) PCT Pub. No.: WO2018/041804
PCT Pub. Date: Mar. 8, 2018

(65) Prior Publication Data
US 2019/0202775 A1    Jul. 4, 2019

(30) Foreign Application Priority Data

Aug. 30, 2016  (EP) .................... 16186393

(51) Int. Cl.
C07C 227/16    (2006.01)
C07C 229/22    (2006.01)

(52) U.S. Cl.
CPC .......... C07C 227/16 (2013.01); C07C 229/22 (2013.01)

(58) Field of Classification Search
CPC .. A61K 47/544; A61K 47/542; A61K 31/352; A61K 47/54; A61K 31/19; C07F 9/10; C08L 101/02; C08L 71/10; C08L 2666/02; C08L 2666/14; C08L 2314/00; Y10S 514/826; C07C 229/22; C07C 227/16; C08G 65/48; C08J 2363/00; C08J 5/24; H05K 1/0326; H05K 3/4626; C07B 2200/07
See application file for complete search history.

(56) References Cited

U.S. PATENT DOCUMENTS 5,227,514 A * 7/1993 Meul ..................... C07C 229/22
560/67

FOREIGN PATENT DOCUMENTS

EP    0553385   *  8/1993

* cited by examiner

Primary Examiner — Yevgeny Valenrod
Assistant Examiner — Blaine G Doletski
(74) Attorney, Agent, or Firm — Medler Ferro Woodhouse & Mills PLLC

(57) ABSTRACT

The present invention relates to a process for preparing 3-(2-hydroxybenzoyloxy)-4-(trimethylammonio)butyrobetaine hydrochloride of formula (I),

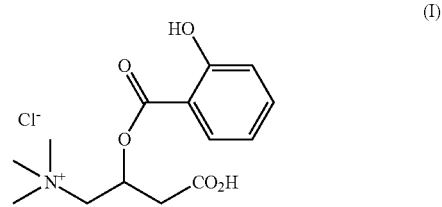

wherein the process comprises reacting 3-hydroxy-4-(trimethylammonio)butyrobetaine or a salt thereof with a 2-alkoxybenzoyl chloride of formula (III),

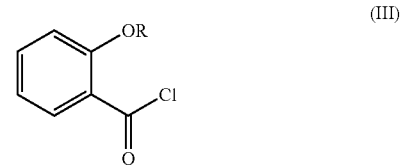

and where R is selected from benzyl and branched C3-C6 alkyl groups.
The present invention further relates to compounds of formula (II) and salts thereof, where R is selected from benzyl and branched C3-C6 alkyl groups, and to a process for preparing same.

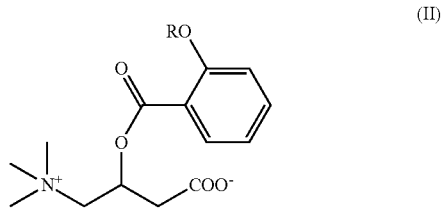

20 Claims, No Drawings

PROCESS FOR PREPARING SALICYLOYL-L-CARNITINE HYDROCHLORIDE

FIELD OF THE INVENTION

The present invention relates in particular to a process for preparing hydroxybenzoyloxy)-4-(trimethylammoino)butyrobetaine hydrochloride of formula (1).

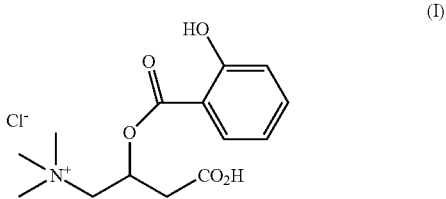 [SMILES: [Cl-] ; C[N+](C)(C)CC(CC(=O)O)OC(=O)c1ccccc1O]

(I)

BACKGROUND OF THE INVENTION 3-(2-Hydroxybenzoyloxy)-4-(trimethylammonio)butyrobetaine hydrochloride, as the ester of salicylic acid with carnitine (salicyloyl carnitine), is a salicylic acid derivative with very promising therapeutic properties (EP 553385). The only known process for preparing salicyloyl carnitine starts with L-carnitine HCl and the acid chloride of salicylic acid, whose hydroxy group is protected by a methyl group. This methyl group can be cleaved only by use of highly concentrated hydrobromic acid. The yield from this cleavage is moderate (50%). In addition, the hydrobromide of salicyloyl carnitine is formed, which for pharmaceutical use must be converted either to free betaine or its hydrochloride, using an ion exchange resin. Over all stages, the yield of salicyloyl carnitine hydrochloride is only 35%.

Therefore, it is an object of the present invention to provide an improved process for preparing 3-(2-hydroxybenzoyloxy)-4-(trimethylammonio)butyrobetaine hydrochloride. In particular, it is an object of the present invention to provide a short and thus cost-effective process, preferably with high yield, for preparing 3-(2-hydroxybenzoyloxy)-4-(trimethylammonio)butyrobetaine hydrochloride.

SUMMARY OF THE INVENTION

It has surprisingly been found that the reaction of carnitine or salts thereof, in particular L-carnitine hydrochloride, with 2-(alkoxy)benzoyl chlorides whose alkoxy groups are cleavable to form the corresponding hydroxy group by the action of hydrochloric acid, in particular and preferably 2-(benzyloxy)benzoyl chloride, 2-(isopropoxy)benzoyl chloride, or 2-(isobutoxy)benzoyl chloride, results in 3-(2-hydroxybenzoyloxy)-4-(trimethylammonio)butyrobetaine hydrochloride of formula (I) in a one-pot process and with a high yield.

Moreover, it has surprisingly been found that the yield of the process according to the invention may be further increased when the reaction that forms the 2-(alkoxy)benzoylcarnitine derivatives of formula (II) as an intermediate product in the one-pot process is facilitated, preferably by applying a vacuum or passing an inert gas through, resulting in removal of the hydrochloric acid that forms. The 3-(2-hydroxybenzoyloxy)-4-(trimethylammonio)butyrobetaine hydrochloride of formula (I) is then preferably formed by subsequent introduction of hydrogen chloride gas. Thus, the process according to the invention even allows the reaction to be stopped at the intermediate stage of the resulting 2-(alkoxy)benzoylcarnitine derivatives of formula (II), and isolation of the 2-(alkoxy)benzoylcarnitine derivatives of formula (II).

In a first aspect of the invention, a process for preparing 3-(2-hydroxybenzoyloxy)-4-(trimethylammonio)butyrobetaine hydrochloride of formula (I) is provided, wherein the process comprises the step (i) reacting 3-hydroxy-4-(trimethylammonio)butyrobetaine or a salt thereof, wherein the salt of 3-hydroxy-4-(trimethylammonio)butyrobetaine is preferably 3-hydroxy-4-(trimethylammonio)butyrobetaine hydrochloride, with a 2-alkoxybenzoyl chloride of formula (III),

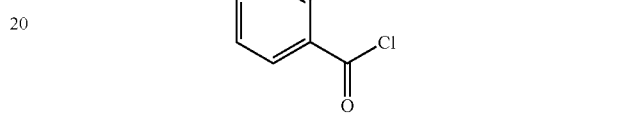

(III)

where R is selected from benzyl and branched C3-C6 alkyl groups.

In a further aspect of the invention, a compound of formula (II) or a salt thereof is provided,

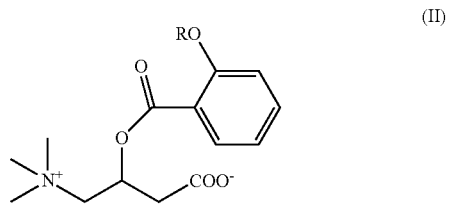

(II)

where R is selected from benzyl and branched C3-C6 alkyl groups.

Further aspects and embodiments of the invention will become apparent in the course of the present description.

DETAILED DESCRIPTION OF THE INVENTION

The term "carnitine" refers to the chemical compound 3-carboxy-2-hydroxypropyl-N,N,N-trimethylammonium hydroxide. The terms "3-hydroxy-4-(trimethylammonio)butyrobetaine," "carnitine," and "3-carboxy-2-hydroxypropyl-N,N,N-trimethylammonium hydroxide" are used synonymously. The compound has an asymmetrical carbon atom, and may therefore occur in two mirror-image optically active forms and as a racemic mixture. "L-carnitine" (L-(−)-carnitine), and thus the (R) enantiomer (R)-(3-carboxy-2-hydroxypropyl)-N,N,N-trimethylammonium hydroxide, is preferred.

The term "betaine" refers to a chemical compound that bears both a positive and a negative charge in its molecular structure, and thus has the outward appearance of being uncharged. In betaines, these charges, unlike the situation with zwitterions, cannot be balanced by proton migration. Carnitine is one example of a betaine.

The term "inert gas" refers to a gas that does not react with either the starting materials or end products, or with the reagents, intermediate products, or solvents, under the given reaction conditions. Typical inert gases are argon and nitrogen, in particular nitrogen.

The terms "reduced pressure" and "vacuum" are used synonymously in the present description, and refer to a pressure inside the reactor in which the process according to the invention is carried out, and which is less than the prevailing atmospheric pressure, for example a pressure of 100-200 mbar.

The term "positive pressure" refers to a pressure inside the reactor in which the process according to the invention is carried out, and which is greater than the prevailing atmospheric pressure, for example a pressure of 2 bar.

The term "C1-C6 carboxylic acid" as used here refers to a organic compound having a chain that contains 1 to 6 carbon atoms and bears one or more carboxy groups (—COOH). The term "C1-C6 carboxylic acid" as used here preferably refers to a monocarboxylic acid, i.e., an organic compound that contains a chain of 1 to 6 carbon atoms and bears a carboxy group. The chain of 1 to 6 carbon atoms typically and preferably refers to a linear or branched, preferably linear, chain of carbon atoms, which may optionally be substituted. Typical and preferred substitutions are in particular halogenated, preferably chlorinated, C1-C6 carboxylic acids. Very preferred "C1-C6 carboxylic acids" for the present invention are monocarboxylic acids containing a linear or branched, preferably linear, saturated chain of carbon atoms, which may optionally be substituted, particularly preferably monocarboxylic acids containing a linear saturated chain of carbon atoms, which may preferably be substituted. Typical and preferred substitutions of this "C1-C6 carboxylic acid" are in particular halogenated, preferably chlorinated, monocarboxylic acids containing a linear saturated chain of carbon atoms.

In a first aspect of the invention, a process for preparing 3-(2-hydroxybenzoyloxy)-4-(trimethylammonio)butyrobetaine hydrochloride of formula (I) is provided, wherein the process comprises the step (i) reacting 3-hydroxy-4-(trimethylammonio)butyrobetaine or a salt thereof, wherein the salt of 3-hydroxy-4-(trimethylammonio)butyrobetaines is preferably 3-hydroxy-4-(trimethylammonio)butyrobetaine hydrochloride, with a 2-alkoxybenzoyl chloride of formula (III),

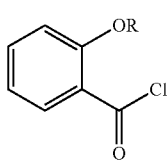

(III)

where R is selected from benzyl and branched C3-C6 alkyl groups. Thus, one advantage of the process according to the invention in particular is that the process according to the invention may be carried out in one step and as a one-pot reaction, which makes the process extremely efficient and more cost-effective.

Of course, depending on the starting material, the process according to the invention is equally suited for the preparation of racemic and optically active 3-(2-hydroxybenzoyloxy)-4-(trimethylammonio)butyrobetaine hydrochloride. In the process according to the invention, the (R)-(−)-3-(2-hydroxybenzoyloxy)-4-trimethylammonio)butyric acid hydrochloride of formula (Ia), starting from (L)-carnitine or a salt thereof, in particular starting from (L)-carnitine hydrochloride, is very particularly preferred.

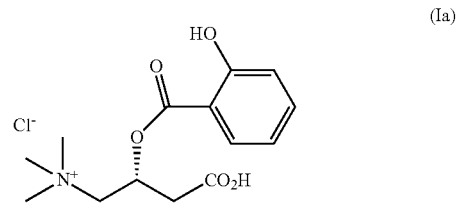 [SMILES: [Cl-] ; C[N+](C)(C)C[C@@H](CC(=O)O)OC(=O)c1ccccc1O]

(Ia)

Therefore, in a further aspect of the invention, a process for preparing (R)-(−)-3-(2-hydroxybenzoyloxy)-4-(trimethylammonio) butyrobetaine hydrochloride of formula (Ia) is provided, characterized in that (R)-(3-hydroxy-4-(trimethylammonio))butyrobetaine ((L)-carnitine) or a salt thereof, preferably the hydrochloride, is reacted with a 2-alkoxybenzoyl chloride of formula (III) (2-alkoxysalicyloyl chloride), where R is selected from benzyl and branched C3-C6 alkyl groups.

In one embodiment, the ratio of said 3-hydroxy-4-(trimethylammonio)butyrobetaine or a salt thereof to said 2-alkoxylbenzoyl chloride of formula (III) is 1:1 to 1:2.5 (mol:mol).

In another embodiment of the process according to the invention, said reaction takes place with 3-hydroxy-4-(trimethylammonio)butyrobetaine and said 2-alkoxybenzoyl chloride of formula (III). In another embodiment of the process according to the invention, said reaction takes place with a salt of 3-hydroxy-4-(trimethylammonio)butyrobetaine, preferably 3-hydroxy-4-(trimethylammonio)butyrobetaine hydrochloride or 3-hydroxy-4-(trimethylammonio)butyrobetaine tartrate, particularly preferably 3-hydroxy-4-(trimethylammonio)butyrobetaine hydrochloride and said 2-alkoxybenzoyl chloride of formula (III).

In another particularly preferred embodiment of the process according to the invention, said reaction includes (i) (1) application of a vacuum; or (2) passing an inert gas through; and wherein the process further comprises step (ii) combining the reaction mixture from said reaction (i) with hydrochloric acid. Said combination of the reaction mixture with hydrochloric acid particularly preferably takes place by introducing gaseous hydrochloric acid.

The yield is surprisingly further increased by this particularly preferred embodiment of the process according to the invention. By applying a vacuum or passing an inert gas through, preferably by applying a vacuum, in the reaction the formation of the 2-(alkoxy)benzoylcarnitine derivatives that are formed as an intermediate product in the one-pot process is facilitated by removal of the hydrochloric acid that forms. The 2-(alkoxy)benzoylcarnitine derivatives of formula (II) that are formed in situ are then converted to the 3-(2-hydroxybenzoyloxy)-4-(trimethylamminio)butyrobetaine hydrochloride of formula (I) by subsequently introducing hydrogen chloride gas. In another particularly preferred embodiment of the present invention, said reaction includes (i) applying a vacuum and carrying out said combination of the reaction mixture with hydrochloric acid (ii) by introducing gaseous hydrochloric acid. Typically and preferably, the application of a vacuum or passing an inert gas through for removing the hydrochloric acid that forms takes place continuously. Also typically and preferably, said reaction (i) is tracked, typically and preferably by thin-layer chromatography. In another preferred embodiment, said combination of the reaction mixture of said reaction (i) with hydrochloric acid, preferably said combination of the reaction mixture with hydrochloric acid by introducing gaseous hydrochloric acid, takes place after 70% reaction, preferably 80% reaction, and particularly preferably 90%, and thus essentially complete, reaction, and also particularly preferably after complete reaction of 3-hydroxy-4-(trimethylammonio)butyrobetaine or a salt thereof, preferably the hydrochloride thereof, with said 2-alkoxybenzoyl chloride of formula (III) to form said intermediate product 2-(alkoxy)benzoylcarnitine derivatives of formula (II). Those skilled in the art are familiar with determining the quantification of the course of said reaction (i).

In another particularly preferred embodiment, said combination of the reaction mixture with hydrochloric acid (ii) includes the addition of water.

The process according to the invention even allows the reaction to be stopped at the intermediate stage of the 2-(alkoxy)benzoylcarnitine derivatives of formula (II) that form, and isolation of the 2-(alkoxy)benzoylcarnitine derivatives of formula (II).

Thus, in a further aspect of the invention, a process for preparing a compound of formula (II) or a salt thereof is provided,

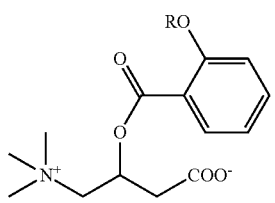

(II)

wherein the process comprises the step (i) reacting 3-hydroxy-4-(trimethylammonio)butyrobetaine or a salt thereof, wherein the salt of 3-hydroxy-4-(trimethylammonio)butyrobetaine is preferably 3-hydroxy-4-(trimethylammonio)butyrobetaine hydrochloride, with a 2-alkoxybenzoyl chloride of formula (III),

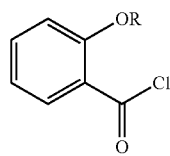

(III)

where R is selected from benzyl and branched C3-C6 alkyl groups; and wherein said reaction (i), typically and preferably for removing the HCl that forms, comprises (1) applying a vacuum; or (2) passing an inert gas through.

Moreover, in a further aspect of the invention a compound of formula (II) or a salt thereof is provided,

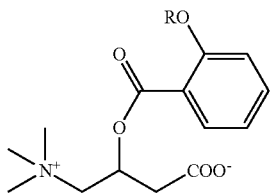

(II)

where R is selected from benzyl and branched C3-C6 alkyl groups.

The isolation of the 2-(alkoxy)benzoylcarnitine derivatives of formula (II) that form results in another embodiment of the present invention, in which the isolated 2-(alkoxy)benzoylcarnitine derivatives of formula (II) are subsequently combined with hydrochloric acid. Thus, in another embodiment of the present invention, said reaction (i) comprises the isolation of an intermediate product of general formula (II) or a salt thereof,

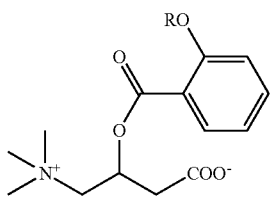

(II)

and said combination of the reaction mixture with hydrochloric acid (ii) is the combination of said intermediate product of general formula (II) or a salt thereof with hydrochloric acid. In one preferred embodiment, said combination of the reaction mixture with hydrochloric acid takes place by introducing gaseous hydrochloric acid.

Thus, the process according to the invention does not necessarily have to be carried out as a one-pot process, which allows a certain flexibility in planning.

In another preferred embodiment, said reaction (i) comprises (1) applying a vacuum, the vacuum being 50 mbar to 800 mbar. In another preferred embodiment, the vacuum is 50 mbar to 700 mbar, preferably 50 mbar to 600 mbar, more preferably 50 mbar to 500 mbar, more preferably 50 mbar to 400 mbar, more preferably 50 mbar to 300 mbar, more preferably 50 mbar to 200 mbar, particularly preferably 100 mbar to 200 mbar, for example 150 mbar.

In another embodiment, said reaction (i) is carried out in a solvent, the solvent being a polar solvent that is inert with respect to hydrochloric acid. In another embodiment, said combination of the reaction mixture with hydrochloric acid (ii) is carried out in a solvent, the solvent being a polar solvent that is inert with respect to hydrochloric acid.

In another embodiment, said reaction (i) is carried out in a solvent, the solvent being a protic, polar solvent that is inert with respect to hydrochloric acid. In another embodiment, said combination of the reaction mixture with hydrochloric acid (ii) is carried out in a solvent, the solvent being a protic, polar solvent that is inert with respect to hydrochloric acid.

In another preferred embodiment, said reaction (i) and said combination of the reaction mixture with hydrochloric acid (ii) are carried out in a solvent, the solvent being a protic, polar solvent that is inert with respect to hydrochloric acid.

In another preferred embodiment, said reaction (i) and said combination of the reaction mixture with hydrochloric acid (ii) are carried out in a solvent, the solvent being selected from aliphatic C1-C6 carboxylic acids, halogenated aliphatic C1-C6 carboxylic acids, and mixtures thereof. In another preferred embodiment, said protic, polar solvent that is inert with respect to hydrochloric acid is selected from halogenated C1-C6 carboxylic acids and mixtures thereof.

In another particularly preferred embodiment, said reaction (i) and said combination of the reaction mixture with hydrochloric acid (ii) are carried out in a solvent, the solvent being selected from halogenated C1-C6 carboxylic acids and mixtures thereof. In another particularly preferred embodiment, the solvent is selected from halogenated acetic acids and mixtures thereof. In another particularly preferred embodiment, said reaction (i) and said combination of the reaction mixture with hydrochloric acid (ii) are carried out in a solvent, the solvent being selected from monochloroacetic acid, dichloroacetic acid, and trichloroacetic acid or mixtures thereof. In another particularly preferred embodiment, said reaction (i) and said combination of the reaction mixture with hydrochloric acid (ii) are carried out in a solvent, the solvent being selected from monochloroacetic acid, dichloroacetic acid, and trichloroacetic acid, the solvent preferably being monochloroacetic acid or dichloroacetic acid, and the solvent particularly preferably being dichloroacetic acid.

In another particularly preferred embodiment, said reaction (i) and said combination of the reaction mixture with hydrochloric acid (ii) are carried out in a solvent, the solvent being a mixture of monochloroacetic acid, dichloroacetic acid, and trichloroacetic acid. In one very particularly preferred embodiment, said reaction (i) and said combination of the reaction mixture with hydrochloric acid (ii) are carried out in a solvent, the solvent being a mixture of monochloroacetic acid and dichloroacetic acid.

In another particularly preferred embodiment, R is selected from benzyl and secondary C3-C6 alkyl groups.

In one particularly preferred embodiment, R is selected from benzyl and secondary C3-C6 alkyl groups, the secondary C3-C6 alkyl group more preferably being selected from isopropyl, sec-butyl, 2-pentyl (sec-pentyl), 3-pentyl, 3-methylbut-2-yl, 2-hexyl, 3-hexyl, 3-methyl-2-pentyl, 4-methyl-2-pentyl, and 3,3-dimethyl-2-butyl, the secondary C3-C6 alkyl group more preferably being selected from isopropyl and sec-butyl, and the secondary C3-C6 alkyl group particularly preferably being isopropyl.

In one particularly preferred embodiment, R is selected from benzyl, isopropyl, sec-butyl, and 2-pentyl (sec-pentyl). In another particularly preferred embodiment, R is selected from benzyl, isopropyl, and sec-butyl (2-butyl). In another particularly preferred embodiment, R is benzyl. In another particularly preferred embodiment, R is isopropyl. In another particularly preferred embodiment, R is sec-butyl (2-butyl).

In another preferred embodiment, said reaction (i) is carried out at a temperature of 20° C. to +30° C. In another preferred embodiment, said reaction (i) is carried out at a temperature of −20° C. to 10° C., −20° C. to 0° C., or −10° C. to 0° C., preferably at a temperature of −10° C. to 0° C.

In another preferred embodiment, said combination of the reaction mixture with hydrochloric acid (ii), preferably the introduction of gaseous hydrochloric acid, is carried out at a temperature of 20° C. to 100° C. In another preferred embodiment, said combination of the reaction mixture with hydrochloric acid (ii), preferably the introduction of gaseous hydrochloric acid, is carried out at a temperature of 20° C. to 100° C., 20° C. to 90° C., 20° C. to 80° C., 20° C. to 60° C., 20° C. to 50° C., or 20° C. to 40° C., preferably at a temperature of 20° C. to 50° C. (25° C. to 45° C., for example).

In another preferred embodiment, said reaction (i) and said combination of the reaction mixture with hydrochloric acid (ii), preferably the introduction of gaseous hydrochloric acid, are carried out at room temperature.

In another preferred embodiment, said combination of the reaction mixture with hydrochloric acid (ii), preferably the introduction of gaseous hydrochloric acid, is carried out under a positive pressure measured at ambient pressure. In one embodiment, said positive pressure is 0.1 to 5 bar, preferably 0.1 to 3 bar, more preferably 0.1 to 2 bar. In another particularly preferred embodiment, said positive pressure is 0.1 to 1 bar.

In one preferred embodiment, said combination of the reaction mixture with hydrochloric acid (ii), preferably the introduction of gaseous hydrochloric acid, and more preferably said reaction (i), and particularly preferably the process according to the invention, are carried out in an autoclave under a positive pressure measured at ambient pressure.

In one typical and preferred embodiment, said positive pressure is generated by the reaction (i) or by said combination of the reaction mixture with hydrochloric acid (ii), preferably by the introduced gaseous hydrochloric acid.

In another particularly preferred embodiment, the process further comprises the step (iii) isolating the 3-(2-hydroxybenzoyloxy)-4-(trimethylammonio)butyrobetaine hydrochloride of formula (I), the isolation taking place by crystallization by adding a nonpolar solvent.

In another particularly preferred embodiment, the process according to the invention includes crystallization of the 3-(2-hydroxybenzoyloxy)-4-(trimethylammonio)butyrobetaine hydrochloride product directly from the reaction mixture by adding a nonpolar solvent.

In another preferred embodiment, said nonpolar solvent has a polarity between 125 kJ/mol and 165 kJ/mol according to the $E_T(30)$ scale (Alan R. Katritzky, Dan C. Fara, Hongfang Yang, Kaido Tämm et al.: Quantitative Measures of Solvent Polarity, p. 183, Spectroscopic Measurements). In one particularly preferred embodiment, said nonpolar solvent is selected from ethyl acetate, diethyl ether, and tert-butyl methyl ether. In another particularly preferred embodiment, said nonpolar solvent is ethyl acetate.

In one particularly preferred embodiment of the process according to the invention, said reaction (i) takes place using (R)-(−)-3-hydroxy-4-(trimethylammonio)butyrobetaine hydrochloride and said 2-alkoxybenzoyl chloride of formula (III). This particularly preferred embodiment of the process according to the invention typically and preferably results in the preparation of (R)-(−)-3-(2-hydroxybenzoyloxy)-4-trimethylammonio)butyric acid hydrochloride of formula (Ia).

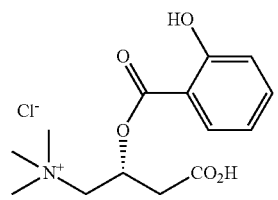

(Ia)

As mentioned, in a further aspect of the invention a compound of formula (II) or a salt thereof is provided,

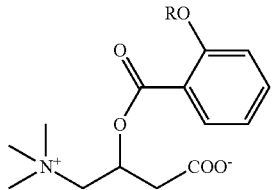

(II)

where R is selected from benzyl and branched C3-C6 alkyl groups.

In one preferred embodiment, the compound of formula (II) according to the invention is selected from 3-(2-(butan-2-yloxy)benzoyloxy)-4-trimethylammonio)butyrobetaine; 3-(2-isopropoxybenzoyloxy)-4-trimethylammonio)butyrobetaine, and 3-(2-benzyloxybenzoyloxy)-4-trimethylammonio)butyrobetaine and salts thereof. In one particularly preferred embodiment, a compound of formula (II) is provided, where R is selected from benzyl, isopropyl, and sec-butyl. In another particularly preferred embodiment, a compound of formula (II) is provided, the compound of formula (II) being selected from 3-(2-(butan-2-yloxy)benzoyloxy)-4-trimethylammonio)butyrobetaine; 3-(2-isopropoxybenzoyloxy)-4-trimethylammonio)butyrobetaine; 3-(2-benzyloxybenzoyloxy)-4-trimethylammonio)butyrobetaine; 3-(2-(butan-2-yloxy)benzoyloxy)-4-trimethylammonio)butyrobetaine hydrochloride; 3-(2-isopropoxybenzoyloxy)-4-trimethylammonio)butyrobetaine hydrochloride; 3-(2-benzyloxybenzoyloxy)-4-trimethylammonio)butyrobetaine hydrochloride; (R)-3-(2-(butan-2-yloxy)benzoyloxy)-4-trimethylammonio)butyrobetaine; (R)-3-(2-isopropoxybenzoyloxy)-4-trimethylammonio)butyrobetaine; (R)-3-(2-benzyloxybenzoyloxy)-4-trimethylammonio)butyrobetaine; (S)-3-(2-(butan-2-yloxy)benzoyloxy)-4-trimethylammonio)butyrobetaine; (S)-3-(2-isopropoxybenzoyloxy)-4-trimethylammonio)butyrobetaine; (S)-3-(2-benzyloxybenzoyloxy)-4-trimethylammonio)butyrobetaine; (R)-3-(2-(butan-2-yloxy)benzoyloxy)-4-trimethylammonio)butyrobetaine hydrochloride; (R)-3-(2-isopropoxybenzoyloxy)-4-trimethylammonio)butyrobetaine hydrochloride; (R)-3-(2-benzyloxybenzoyloxy)-4-trimethylammonio)butyrobetaine hydrochloride; (S)-3-(2-(butan-2-yloxy)benzoyloxy)-4-trimethylammonio)butyrobetaine hydrochloride; (S)-3-(2-isopropoxybenzoyloxy)-4-trimethylammonio)butyrobetaine hydrochloride; and (S)-3-(2-benzyloxybenzoyloxy)-4-trimethylammonio)butyrobetaine hydrochloride.

EXAMPLES

The invention is explained in greater detail in the following non-limiting examples.

Example 1

(R)-(−)-3-(2-hydroxybenzoyloxy)-4-trimethylammonio)butyric acid hydrochloride 8.5 g 2-benzyloxybenzoyl chloride was added dropwise to a mixture of 12.0 g monochloroacetic acid, 6.4 g dichloroacetic acid, and 3.0 g L-carnitine hydrochloride at 20-25° C. over a period of 10 minutes. The reaction mixture was stirred for 15 hours at 20-25° C. and subsequently diluted with 120 mL diethyl ether. The precipitated product was filtered off with suction and dried under vacuum at 20-25° C.

Yield: 6.0 g

Melting point: 184-185° C. (after recrystallization from ethanol/ethyl acetate)

Example 2

(R)-(−)-3-(2-hydroxybenzoyloxy)-4-trimethylammonio)butyric acid hydrochloride 9.9 g L-carnitine hydrochloride was dissolved in 50.0 g dichloroacetic acid at 60-65° C. 20.9 g 2-isopropoxybenzoyl chloride was added dropwise to this solution at −10 to 0° C. over a period of 60 minutes. During the dropwise addition and the subsequent secondary reaction at −10 to 0° C., the released hydrogen chloride gas was expelled from the reaction mixture by application of a slight vacuum (100-200 mbar). The reaction was tracked by DC (silica gel; eluent: chloroform:methanol:water:5% ammonia solution (55:39:1:5)). After approximately 1 hour, 9.4 g gaseous hydrochloric acid was introduced into the reaction solution. The reaction solution was heated at 45-50° C. for 30 minutes, a small quantity of water was added, and the reaction solution was further stirred at 20 to 25° C. The reaction was once again tracked by DC (silica gel; eluent: chloroform:methanol:water:5% ammonia solution (55:39:1:5)). The reaction mixture was then diluted with 200 mL ethyl acetate and inoculated with salicyloyl-L-carnitine HCl. As soon as the product began to crystallize, an additional 200 mL of ethyl acetate was added. The resulting suspension was cooled to 10 to 15° C., and stirring was performed for another hour at this temperature. The product that crystallized out was filtered off with suction, washed with 100 mL ethyl acetate, and dried overnight in a vacuum drying oven at 40-45° C.

Yield: 14.6 g (92%)

Melting point: 184-185° C.

RF: 0.19 (silica gel; eluent: chloroform:methanol:water: 5% $NH_3$ solution (55:39:1:5))

$[\alpha]_D^{20}$=−25.6° (c=1, water)

Example 3

(R)-(−)-3-(2-isopropoxybenzoyloxy)-4-trimethylammonio)butyric acid 5.0 g L-carnitine hydrochloride was dissolved in 28.0 g trifluoroacetic acid at 40-45° C. 11 g 2-isopropoxybenzoyl chloride was added dropwise to this solution at 0-20° C. over a period of 20 minutes. During the dropwise addition and the subsequent secondary reaction at 0-20° C., a nitrogen stream was led through the solution in order to expel the released hydrogen chloride gas. The reaction was tracked by DC (silica gel; eluent: chloroform:methanol:water:5% ammonia solution (55:39:1:5)). After approximately 1 hour, the reaction solution was quenched by adding 100 mL tert-butyl methyl ether. The precipitated product was taken up in 10 mL water, filtered over a column containing a weakly basic ion exchange resin, and concentrated under vacuum. The obtained solid was recrystallized from acetonitrile/acetone.

Yield: 5.6 g $[\alpha]_D^{20}$=−14.2° (c=1, water)

Melting point: 142-144° C.

RF: 0.28 (silica gel; eluent: chloroform:methanol:water: 5% $NH_3$ solution (55:39:1:5)) 1H-NMR (DMSO-d6, 300 MHz)

δ: 7.61-6.95 (m, 4H)
5.69-5.57 (m, 1H)
4.76-4.62 (m, 1H)
3.89-3.68 (m, 2H)
3.14 (s, 9H)
2.43-2.09 (m, 2H)
1.27 (d, 6H)
MS: 323 (M+1)

Example 4

R)-(−)-3-(2-(butan-2-yloxy)benzoloxy)-4-trimethyl-ammonio)butyric acid 4.0 g L-carnitine was dissolved in 40.0 g dichloroacetic acid at 40-45° C. 13.2 g 2-sec-butoxybenzoyl chloride was added dropwise to this solution at 0-20° C. over a period of 20 minutes. During the dropwise addition and the subsequent secondary reaction at 0-20° C., a nitrogen stream was led through the solution in order to expel the released hydrogen chloride gas. The reaction was tracked by DC (silica gel; eluent:chloroform:methanol:water: 5% ammonia solution (55:39:1:5)). After approximately 1.5 hours, the reaction solution was quenched by adding 300 mL tert-butyl methyl ether. The precipitated product was taken up in 15 mL water, filtered over a column containing a weakly basic ion exchange resin, and concentrated under vacuum. The obtained solid was recrystallized from acetonitrile/acetone.

Yield: 3.2 g
$[\alpha]_D^{20}=-22.6°$ (c=1, water)
Melting point: 134-135° C.
1H-NMR of the main diastereomer (DMSO-d6, 300 MHz)
δ: 7.63-6.94 (m, 4H)
5.69-5.57 (m, 1H)
4.53-4.41 (m, 1H)
3.89-3.65 (m, 2H)
3.14 (s, 9H)
2.43-2.09 (m, 2H)
1.70-1.51 (m, 2H)
1.24-1.21 (m, 3H)
0.95-0.89 (m, 3H)
MS: 338 (M+1)

The invention claimed is:
1. A process for preparing 3-(2-hydroxybenzoyloxy)-4-(trimethylammonio)butyrobetaine hydrochloride of formula (I),

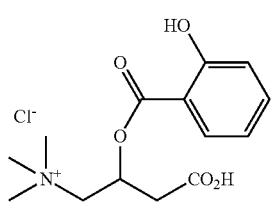

wherein the process comprises the step
(i) reacting 3-hydroxy-4-(trimethylammonio)butyrobetaine or a salt thereof, the with a 2-alkoxybenzoyl chloride of formula (III),

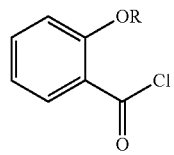

where R is selected from benzyl and branched C3-C6 alkyl groups.

2. The process according to claim 1, wherein said reaction (i) comprises
(1) applying a vacuum; or
(2) passing an inert gas through;
and wherein the process further comprises the step
(ii) combining the reaction mixture, of said reaction (i), with hydrochloric acid.

3. The process according to claim 2, wherein said reaction (i) comprises isolating an intermediate product of formula (II) or a salt thereof,

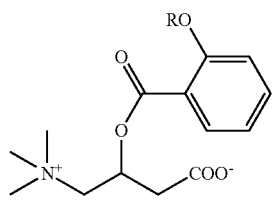

and said combination of the reaction mixture with hydrochloric acid (ii) is the combination of said intermediate product of formula (II) or a salt thereof with hydrochloric acid.

4. The process according to claim 2, wherein said reaction (i) comprises application of a vacuum, and wherein the vacuum is 50 mbar to 800 mbar.

5. The process according to claim 2, wherein said reaction (i) and said combination of the reaction mixture with hydrochloric acid (ii) are carried out in a solvent, the solvent being a protic, polar solvent that is inert with respect to hydrochloric acid.

6. The process according to claim 5, wherein said protic, polar solvent that is inert with respect to hydrochloric acid is selected from halogenated C1-C6 carboxylic acids and mixtures thereof.

7. The process according to claim 1, wherein R is selected from benzyl and secondary C3-C6 alkyl groups.

8. The process according to claim 7, wherein R is selected from benzyl, isopropyl, sec-butyl, and 2-pentyl (sec-pentyl).

9. The process according to claim 1, wherein said reaction (i) is carried out at a temperature of 20° C. to +30° C.

10. The process according to claim 2, wherein said combination of the reaction mixture with hydrochloric acid (ii) is carried out at a temperature of 20° C. to 100° C.

11. The process according to claim 2, wherein said combination of the reaction mixture with hydrochloric acid (ii) is carried out under a positive pressure measured at ambient pressure.

12. The process according to claim 1, wherein the process further comprises the step
(iii) isolating the 3-(2-hydroxybenzoyloxy)-4-(trimethylammonio)butyrobetaine hydrochloride of formula (I), wherein the isolation takes place by crystallization by adding a nonpolar solvent.

13. The process according to claim 1, wherein said reaction (i) takes place with (R)-(−)-3-hydroxy-4-(trimethylammonio)butyrobetaine hydrochloride and said 2-alkoxybenzoyl chloride of formula (III).

14. A process for preparing a compound of formula (II), or a salt thereof,

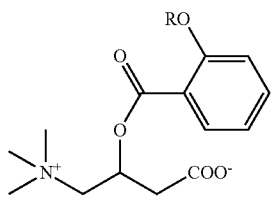

wherein the process comprises the step
(i) reacting 3-hydroxy-4-(trimethylammonio)butyrobetaine or a salt thereof, the with a 2-alkoxybenzoyl chloride of formula (III),

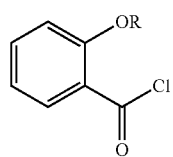

where R is selected from benzyl and branched C3-C6 alkyl groups.

15. A compound of formula (II) or a salt thereof,

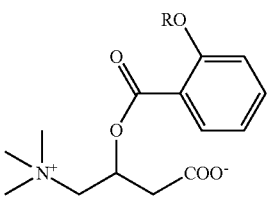

where R is selected from benzyl and branched C3-C6 alkyl groups.

16. The process of claim 1, wherein the salt of 3-hydroxy-4-(trimethylammonio)butyrobetaine is 3-hydroxy-4-(trimethylammonio)butyrobetaine hydrochloride.

17. The process of claim 14, wherein the salt of 3-hydroxy-4-(trimethylammonio)butyrobetaine is 3-hydroxy-4-(trimethylammonio)butyrobetaine hydrochloride.

18. The process of claim 14, and wherein for removal of the HCl that forms, said reaction (i) comprises
(1) applying a vacuum; or
(2) passing an inert gas through.

19. The process of claim 2, wherein the process further comprises the step
(iii) isolating the 3-(2-hydroxybenzoyloxy)-4-(trimethylammonio)butyrobetaine hydrochloride of formula (I), wherein the isolation takes place by crystallization by adding a nonpolar solvent.

20. The process of claim 2, wherein said reaction (i) takes place with (R)-(−)-3-hydroxy-4-(trimethylammonio)butyrobetaine hydrochloride and said 2-alkoxybenzoyl chloride of formula (III).

* * * * *